United States Patent
Matthiessen et al.

(10) Patent No.: US 7,339,669 B2
(45) Date of Patent: Mar. 4, 2008

(54) DEVICE FOR THE ANALYSIS OF THE QUALITATIVE COMPOSITION OF GASES

(75) Inventors: Hans Matthiessen, Bad Schwartau (DE); Gerd Peter, Lübeck (DE); Axel Lamprecht, Lübeck (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 23 days.

(21) Appl. No.: 11/268,242

(22) Filed: Nov. 7, 2005

(65) Prior Publication Data

US 2006/0158648 A1 Jul. 20, 2006

(30) Foreign Application Priority Data

Jan. 14, 2005 (DE) .................... 10 2005 002 106

(51) Int. Cl.
*G01J 3/28* (2006.01)
(52) U.S. Cl. ...................... 356/326; 356/328
(58) Field of Classification Search .......... 359/83, 359/599; 356/326, 328, 432, 436, 437; 250/343

See application file for complete search history.

(56) References Cited

U.S. PATENT DOCUMENTS

| | | | | |
|---|---|---|---|---|
| 4,678,332 A | * | 7/1987 | Rock et al. | 356/328 |
| 5,070,245 A | * | 12/1991 | Rantala et al. | 250/343 |
| 5,444,528 A | * | 8/1995 | Puschell | 356/73 |
| 5,479,258 A | * | 12/1995 | Hinnrichs et al. | 356/326 |
| 5,581,405 A | * | 12/1996 | Meyers et al. | 359/571 |
| 5,867,264 A | * | 2/1999 | Hinnrichs | 356/310 |
| 5,905,571 A | * | 5/1999 | Butler et al. | 356/328 |
| 6,100,974 A | * | 8/2000 | Reininger | 356/300 |
| 6,101,034 A | * | 8/2000 | Cox et al. | 359/562 |
| 6,741,349 B1 | * | 5/2004 | Sweatt et al. | 356/328 |
| 6,816,258 B2 | * | 11/2004 | Hutchin | 356/328 |

(Continued)

FOREIGN PATENT DOCUMENTS

DE 44 34 814 4/1996

(Continued)

OTHER PUBLICATIONS

W. A. Traub, "Constant-dispersion grism spectrometer for channeled spectra," J. Opt. Soc. Am. A, vol. 7, pp. 1779-1791 (1990).*

(Continued)

*Primary Examiner*—Tarifur Chowdhury
*Assistant Examiner*—Jonathan M Hansen
(74) *Attorney, Agent, or Firm*—McGlew and Tuttle P.C.

(57) ABSTRACT

A device for the analysis of the qualitative, optionally also the quantitative composition of gases, uses measuring light of known spectral composition that can pass through the gas to be analyzed and the gas can be caused to interact. A detector arrangement is present, which can detect light originating from the sites of the interaction between the measuring light and the gas to be analyzed. At least one refractive-diffractive optical element is provided, which is transparent over its entire surface and contributes to a wavelength-dependent imaging of the light to be detected onto the detector arrangement in a transmitting manner. The refractive-diffractive optical element is arranged in the ray path between the area in which the interaction between the gas to be analyzed and the measuring light takes place and the detector arrangement.

23 Claims, 2 Drawing Sheets

U.S. PATENT DOCUMENTS

| | | | |
|---|---|---|---|
| 6,903,329 B2 * | 6/2005 | Gentala ....................... 250/238 |
| 2002/0141702 A1 * | 10/2002 | Ojima et al. ................... 385/37 |
| 2003/0043373 A1 * | 3/2003 | Russell ....................... 356/328 |
| 2003/0086091 A1 * | 5/2003 | Hinnrichs et al. ........... 356/436 |
| 2003/0231308 A1 * | 12/2003 | Granger ....................... 356/326 |
| 2004/0070853 A1 * | 4/2004 | Ebizuka et al. ............. 359/833 |
| 2004/0160673 A1 * | 8/2004 | Se et al. ...................... 359/599 |
| 2004/0227939 A1 * | 11/2004 | Granger ....................... 356/326 |
| 2006/0067611 A1 * | 3/2006 | Frisken et al. ................ 385/16 |
| 2006/0181705 A1 * | 8/2006 | Cunningham et al. ...... 356/326 |

FOREIGN PATENT DOCUMENTS

| DE | 196 47 632 | 11/1997 |
|---|---|---|
| DE | 103 15 864 | 11/2004 |

OTHER PUBLICATIONS

L. Weitzel et al., "3D: The next generation near-infrared imaging spectrometer", Astron. Astrophys. Suppl. Ser. 119, pp. 531-546 (1996).*

Kosterev, Anatoliy A., "Chemical Sensors Based on Quantum Cascade Lasers", IEEE Journal of Quantum Electronics, vol. 38, No. 6, Jun. 2002, pp. 582-291.*

* cited by examiner

DEVICE FOR THE ANALYSIS OF THE QUALITATIVE COMPOSITION OF GASES

CROSS REFERENCE TO RELATED APPLICATIONS

This application claims the benefit of priority under 35 U.S.C. § 119 of German Application DE 10 2005 002 106.9 filed Jan. 14, 2005, the entire contents of which are incorporated herein by reference.

FIELD OF THE INVENTION

The present invention pertains to a device for the analysis of the qualitative composition of gases with spectroscopic means.

BACKGROUND OF THE INVENTION

Many different methods can be used for the analysis of gases. Among other things, infrared optical sensors have become established, which have relatively low cross sensitivities and are characterized by high reliability. This type of sensor is therefore used in both medical engineering, for example, for the analysis of gaseous anesthetics, $CO_2$ or dinitrogen monoxide, and safety engineering for the detection of hydrocarbons, carbon dioxide, etc.

Infrared optical sensors are based on the evaluation of spectral changes, which are caused by interactions of gases being analyzed with a measuring light. The spectrum of the measuring light may change due to absorption processes or spontaneous emission may occur after an interaction. It is necessary in most applications to detect and/or evaluate changes in markedly narrower wavelength intervals from a relatively broad-band spectrum in the infrared range. Spectral selection is necessary in these cases.

Distinction is made among the infrared optical sensors between dispersing and nondispersing systems. Dispersing systems often contain classical grid structures and have the advantage of using a larger amount of spectral information due to a wavelength-dependent splitting, but, on the other hand, instruments with such devices are mostly very expensive, relatively large and cumbersome to handle. Even though nondispersing systems are mostly more robust and more compact, it is frequently impossible to go below a certain cost limit due to the use of relatively expensive interference filters, precisely when a larger number of detectors (>2) is used.

Moreover, additional lens systems are frequently used for focusing with both methods, and these lens systems make such sensors more expensive and less compact.

However, focusing frequently cannot be done away with. To make additional focusing elements dispensable, it is known that attempts have been made to design dispersing elements macroscopically such that they possess focusing and imaging properties. Spherical concave structures, whose surface is periodically microstructured, may be mentioned as examples of this. As a result, an optical element is obtained, which combines the imaging properties of a hollow mirror with the dispersing action of a reflection grid. However, such elements require a large amount of material for their manufacture, and are difficult and expensive to manufacture. In addition, a markedly longer ray path to the site of detection is frequently associated with the use of such reflectively operated elements, as a result of which the probability that the signal to be evaluated is distorted by effects unrelated to the analyte increases.

SUMMARY OF THE INVENTION

The object of the present invention is to provide a device for preferably infrared optical gas analysis, which can be manufactured at low cost, has a high sensitivity and a compact and lightweight design and is characterized by a high level of safety against distortions of the measured signal.

According to the invention, a device for the analysis of the qualitative composition of gases is provided in which measuring light of a known spectral composition can pass through the gas to be analyzed and the gas can be caused to interact. A detector arrangement is present, which can detect light emitted from the sites of interaction between the measuring light and the gas to be detected. At least one refractive-diffractive optical element is transparent over its entire surface and contributes in a transmitting manner to the wavelength-dependent imaging of the light to be detected on the detector arrangement. The refractive-diffractive optical element is arranged in the ray path between the area in which the interaction takes place between the gas to be analyzed and the measuring light and the detector arrangement.

The present invention is based on the fact that it is possible to use, at least for the qualitative analysis of gases, a refractive-diffractive optical element (RDOE), which is used in the transmitting manner and achieves an imaging action, without being shaped macroscopically as a classical lens.

The present invention comprises a device for the analysis of at least the qualitative composition of gases, in which measuring light of a known spectral composition can pass through the gas to be analyzed, the gas to be analyzed can be caused to interact and in which a detector arrangement is present, which can detect light emitted from the sites of the interaction between the measuring light and the gas to be analyzed; The at least one refractive-diffractive optical element, which is transparent over its entire surface and contributes to a wavelength-dependent imaging of the light to be detected onto the detector arrangement in a transmitting manner, is arranged in the ray path between the area in which the interaction between the gas to be analyzed and the measuring light takes place and the detector arrangement.

An RDOE in terms of the present invention is a preferably planar body, which consists essentially of a transparent material and which has a structured surface at least on one side. The structuring is performed such that abrupt changes occur in the thickness of the transparent material, which changes in thickness are distributed over the structured surface and ensure a dispersing action, similarly to a phase grid. In addition, the surface is microstructured at least in individual areas in such a way that ensures the imaging action of the individual surface areas or of the entire structure. This microstructuring may contain a curvature of the individual surface areas and/or the formation of microscopically small, optically active structures on the order of magnitude of the wavelengths used, for example, prisms.

At any rate, it is advantageous that the optical element has both dispersing action and focusing action, that it does not have to have macroscopically any appreciable differences in thickness and that it operates in transmission. As a result, a compact design and short distances between the site of the gas to be analyzed, the RDOE and the detector arrangement can be achieved, which in turn reduces the susceptibility to trouble of the device. Moreover, a planar basic shape of the RDOE makes possible a flat and consequently outright lightweight design.

Very inexpensive manufacture is achieved if the RDOE is manufactured from a directly structurable blank.

Due to the dispersing action being achieved exclusively by thickness differences of the material of the basic body, it is not necessary to reduce the transparency of individual surface areas, as it happens, e.g., in the case of amplitude grids. Thus, the entire cross section of the RDOE is available for collecting the light to be guided to the detector arrangement. This maximizes the measuring sensitivity of the device according to the present invention.

The RDOE has a dispersing character and is at the same time able, like a classical refractive lens, to produce a focus. The location of the focal points depends on the wavelength. The figure along which the focus is displaced during a change in wavelength can be set by the structure of the RDOE. It is possible as a result to adapt the imaging geometry to preferred or design-dependent detector arrangements. Thus, the device according to the present invention may be advantageously designed such that a plurality of detector elements are arranged in one plane or even three-dimensionally. Depending on the embodiment, it is possible to use double detectors, detector cells or 2D chips instead of individual detector elements, as a result of which a plurality of wavelengths can be analyzed simultaneously.

Whether the device according to the present invention can be used only for a qualitative gas analysis or whether it also makes quantitative evaluations possible depends on the further processing of the signals sent by the individual detector elements. The signal processing can be performed extensively according to known algorithms for spectral analysis, which applies to both the evaluation of the emission of excited gases and the analysis of the absorption of the gas to be analyzed.

A plurality of refractive-diffractive elements, which are suitable for the imaging of different wavelength ranges, may be advantageously contained.

Especially lightweight designs can be embodied if one or more refractive-diffractive optical elements consist of a plastic. However, most plastics are ruled out for the manufacture of infrared-transparent optical elements because of their absorption properties. However, it was found that thanks to the appropriate selection of the material, refractive-diffractive optical elements may consist of a plastic that has a transmission of T>50% in the wavelength range of 3 µm to 12 µm at the used thickness of the RDOE, which is on the order of magnitude of a few mm. This is sufficient for devices according to the present invention in most cases.

It is especially advantageous to make devices according to the present invention with RDOEs made of polyethylene. This material makes possible at the same time the use of advantageous methods of surface structuring, which make possible the markedly more inexpensive structuring and manufacture of the RDOEs, compared to other materials, by corresponding replication methods (hot embossing method, injection molding, etc.) in conjunction with lower raw material costs.

Furthermore, plastics have a relatively great thermal expansion. Thus, PE has an expansion that is about 14 times greater at a given temperature change than that of gold. Since the expansion takes place isotropically, this property can be utilized, to a certain extent, in RDOEs designed as surface elements to coordinate the optical properties of these elements, by a specific temperature change, e.g., in order to absorb manufacturing tolerances. It may therefore be advantageous if means are present that make it possible to maintain the temperature of at least one refractive-diffractive optical element or to maintain it at presettable values. These means may comprise, for example, heatable holding structures and/or advantageous encapsulations of the RDOEs.

It may be advantageous for design reasons if the detector arrangement comprises at least one movably arranged detector, which can be moved in a controlled manner in the imaging area or if other means are present that make it possible to achieve a relative movement between the detector arrangement and the refractive-diffractive optical element. The figure to be traveled is advantageously adapted to the position of the wavelength-dependent focal points.

An alternative application of the concept according to the present invention may be to arrange a plurality of RDOEs on a support, for example, on a plastic support, in the form of a segmented lens array, which illuminates a corresponding detector arrangement.

The present invention will be explained on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
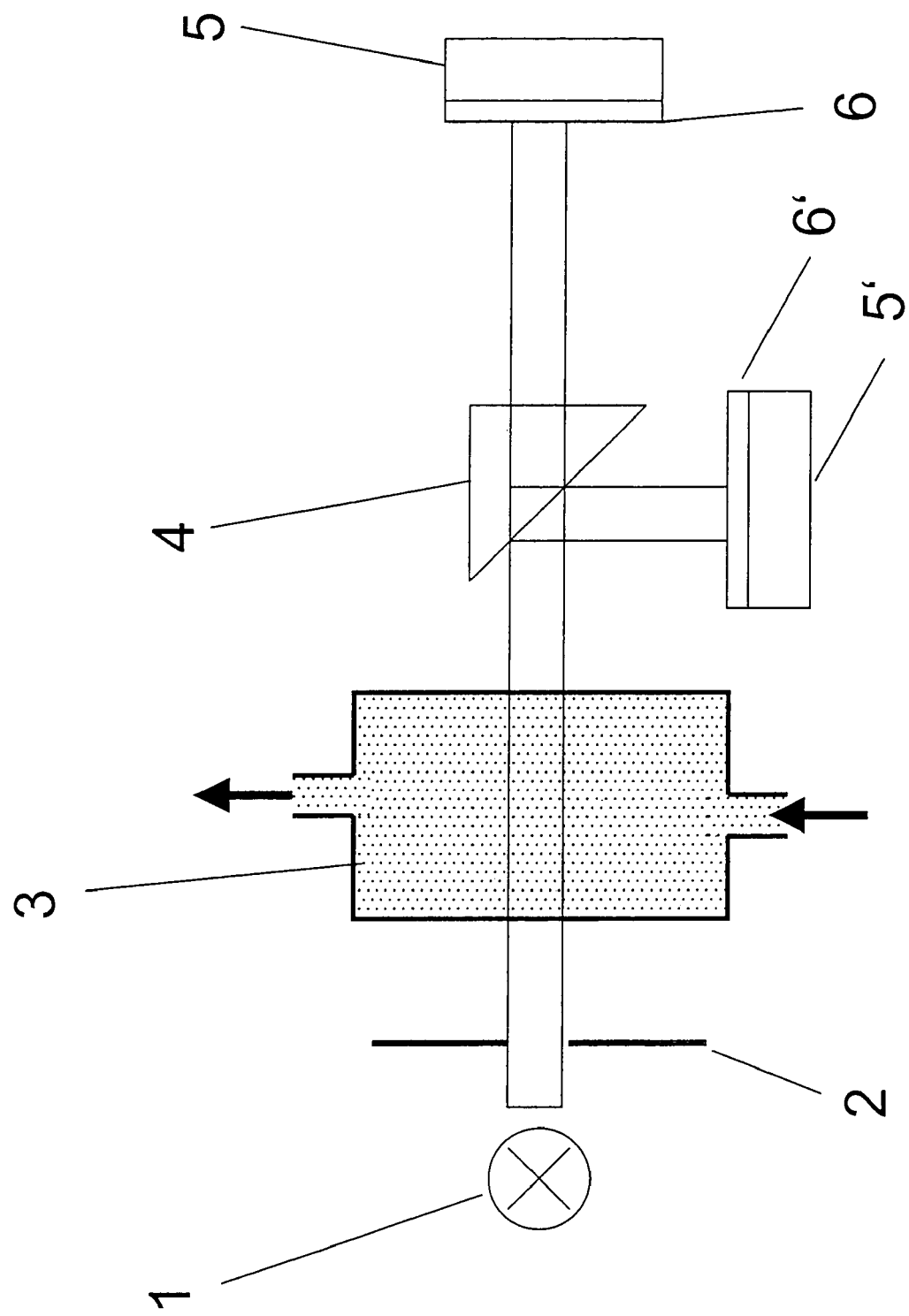
FIG. 1 is a schematic view of an IR sensor according to the present invention.

Referring to the drawings in particular, in FIG. 1, a light source 1 is shown sending measuring light in the infrared spectral range. The measuring light passes through a diaphragm 2 and an absorption chamber 3 before it reaches a beam splitter 4. The gas to be analyzed is sent through the absorption chamber 3. As a result, interactions will take place between the gas to be analyzed and the measuring light, which can lead to absorption and/or emission effects. Components of the light exiting from the absorption chamber 3 are deflected by the beam splitter 4 to detectors 5, 5', in front of which interference filters 6, 6' are arranged, which ensure that only light of the wavelength range that is to be detected by the particular detector 5, 5' will indeed generate a signal.

Figure 2:
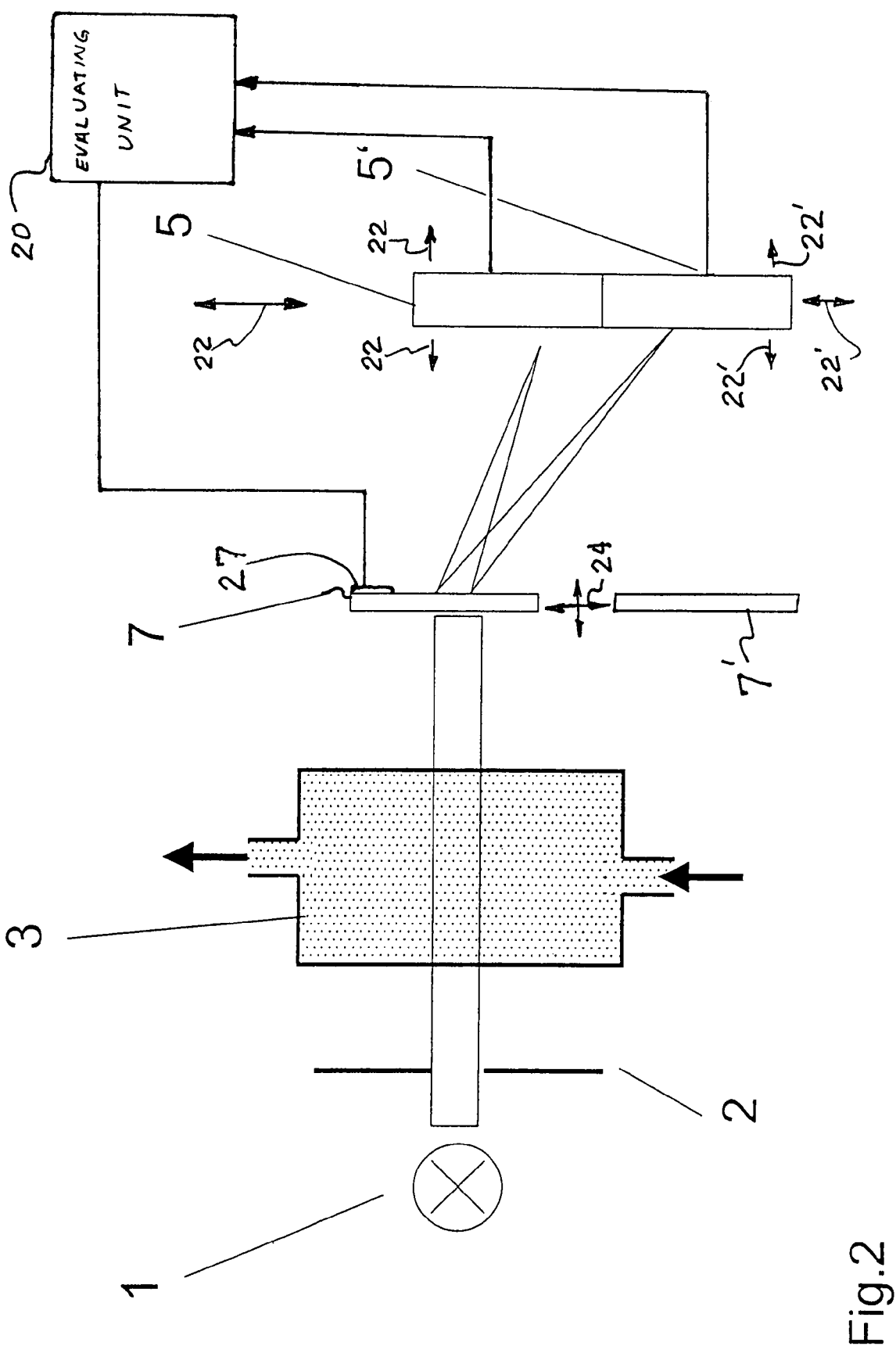
FIG. 2 is a schematic view of an IR sensor with a refractive-diffractive optical element.

FIG. 2 shows the schematic view of a device according to the present invention, an IR sensor with a refractive-diffractive optical element (RDOE) 7. This likewise has an arrangement comprising a light source 1, a diaphragm 2 and an absorption chamber 3. However, the light exiting from the absorption chamber 3 is sent through a transparent refractive-diffractive optical element 7 made of polyethylene rather than to a beam splitter. This leads to a wavelength-dependent imaging on detectors 5, 5', which are arranged in a plane extending at right angles to the optical axis. It is not necessary to provide the detectors with filters, because the wavelength dependence of the imaging already ensures "geometric filtration". One advantage is that due to the elimination of a beam splitter, the total amount of energy available at a wavelength of interest is always collected in a focal point to be assigned to that wavelength and is available for the detection.

Due to the dispersing character of the RDOE 7, light exiting from the absorption chamber 3 is split in a wavelength-dependent manner and is focused on the detector elements 5, 5' due to the additional focusing properties. At least another refractive-diffractive optical element 7' may be provided so there are a plurality of refractive-diffractive optical elements 7, 7', each of which is suitable for imaging different wavelength ranges. Advantageously, the plurality of detector elements 5, 5' are arranged in one plane or in multiple plane (three dimensional array). Detector 5 may be provided as a movably arranged detector 5, which can be moved in a controlled manner in the imaging area as shown at 22. Detector 5' may also be provided as a movably arranged detector 5', which can be moved in a controlled manner in the imaging area as shown at 22'. Additionally, the system may have other means that make it possible to achieve a relative movement 24 between the detector arrangement 5, 5' and the refractive-diffractive optical element 7. The course traveled by the detector 5 is advantageously adapted to the position of the wavelength-dependent focal points.

The device may include an evaluation unit 20 that provides a means that make possible the quantitative evaluation of the detected signals. This may evaluating unit 20 may also comprise means for the evaluation of spontaneous emission. The unit 20 may further comprise a means for the evaluation of the absorption of the gas to be analyzed. A heating element 27 or other means are present which make it possible to set the temperature of at least one refractive-diffractive optical element 7 or to maintain it at presettable values and monitor temperature of the refractive-diffractive optical element 7. This may be controlled by the evaluating unit 20 or microprocessor associated with the evaluating unit 20.

While specific embodiments of the invention have been shown and described in detail to illustrate the application of the principles of the invention, it will be understood that the invention may be embodied otherwise without departing from such principles.

What is claimed is:

1. A device for the analysis of the qualitative composition of gases, in which measuring light of a known spectral composition can pass through the gas to be analyzed and the gas can be caused to interact, the device comprising:
   a first detector element having a first emitted light wavelength detection range, said first detector element being positioned to detect light emitted from areas of interaction between the measuring light and the gas to be analyzed;
   a second detector element having a second emitted light wavelength detection range, said second detector element being positioned to detect light emitted from areas of interaction between the measuring light and the gas to be analyzed, said second emitted light wavelength detection range being different than said first emitted light wavelength detection range;
   at least one refractive-diffractive optical element, said at least one refractive-diffractive optical element dispersing light onto said first detector element in a wavelength dependent manner, said at least one refractive-diffractive optical element dispersing the light onto said second detector element in a wavelength dependent manner, said at least one refractive-diffractive optical element focusing light on said first detector element, said at least one refractive-diffractive optical element focusing light on said second detector element, said at least one refractive-diffractive optical element being transparent over an entire surface thereof, said at least one refractive-diffractive optical element being arranged in a ray path between the area in which the interaction takes place between the gas to be analyzed and the measuring light and said first detector element and said second detector element.

2. A device in accordance with claim 1, further comprising means for evaluating the detected signals.

3. A device in accordance with claim 1, further comprising means for the evaluation of spontaneous emission.

4. A device in accordance with claim 1, further comprising means for the evaluation of the absorption of the gas to be analyzed.

5. A device in accordance with claim 1, wherein said plurality of detector elements are arranged in one plane.

6. A device in accordance with claim 1, wherein said plurality of detector elements are arranged three-dimensionally.

7. A device in accordance with claim 1, further comprising at least another refractive-diffractive optical element to provide a plurality of refractive-diffractive optical elements, each of which is suitable for imaging different wavelength ranges.

8. A device in accordance with claim 1, wherein said at least one refractive-diffractive optical element consists of a plastic.

9. A device in accordance with claim 1, wherein said at least one refractive-diffractive optical element consists of a plastic that has a transmission of T>50% in the wavelength range from 3 µm to 12 µm at the used thickness of the RDOE.

10. A device in accordance with claim 1, wherein said at least one refractive-diffractive optical element consists of polyethylene.

11. A device in accordance with claim 1, wherein one of said first and second detector elements and said refractive-diffractive optical elements is movably arranged relative to the other.

12. A device in accordance with claim 1, wherein means are present which make it possible to set the temperature of at least one refractive-diffractive optical element or to maintain it at presettable values.

13. A gas analysis device comprising:
   a measuring light source of a known spectral composition;
   an absorption chamber with a space for gas to be analyzed, the measuring light being directed to pass through the gas to be analyzed and the gas interacting at an area in which the interaction takes place;
   a first detector element having a first emitted light wavelength detection range, said first detector element being positioned to detect light emitted from areas of interaction between the measuring light and the gas to be detected;
   a second detector element having a second emitted light wavelength detection range, said second detector element being positioned to detect light emitted from areas of interaction between the measuring light and the gas to be detected;
   a refractive-diffractive optical element that is transparent over an entire surface thereof and contributing in a transmitting manner to a wavelength-dependent imaging of the light to be detected on the first detector element and the second detector element including dispersing light in a wavelength dependent manner including light directed at first detector element and focused thereon and dispersing light directed at said second detector element and focused thereon, said refractive-diffractive optical element being arranged in a ray path between the area in which the interaction between the gas to be analyzed and the measuring light takes place and said first and second detector elements whereby a qualitative analysis of the composition of gases may be provided.

14. A device in accordance with claim 13, further comprising an evaluation unit for receiving data signals from said detector elements to provide a quantitative evaluation of the detected signals.

15. A device in accordance with claim 13, further comprising an evaluation unit for receiving data signals from said detector elements and further comprising means for the evaluation of a spontaneous emission.

16. A device in accordance with claim 13, further comprising an evaluation unit for receiving data signals from said detector elements for the evaluation of the absorption of the gas to be analyzed.

17. A device in accordance with claim 13, wherein said detector elements are arranged in one plane.

18. A device in accordance with claim 13, wherein said detector elements are arranged three-dimensionally.

19. A device in accordance with claim 13, further comprising another refractive-diffractive optical element to provide a plurality of refractive-diffractive optical elements, each of which is suitable for imaging different wavelength ranges.

20. A device in accordance with claim 13, wherein said at least one refractive-diffractive optical element consists of a plastic.

21. A device for the analysis of the qualitative composition of gases, in which measuring light of a known spectral composition can pass through the gas to be analyzed and the gas can be caused to interact, the device comprising:

a detector arrangement including a first detecting element having a first wavelength detection range and a second detecting element having a second wavelength detection range, said first detecting element and said second detecting element detecting light emitted from sites of interaction between the measuring light and the gas to be detected;

a refractive-diffractive optical element, said refractive-diffractive optical element being transparent over an entire surface thereof and contributing in a transmitting manner to a wavelength-dependent imaging of the light to be detected on said first detecting element and said second detecting element including dispersing light in a wavelength dependent manner that light is directed at said first detecting element and focused thereon and light is directed at said second detecting element and focused thereon, whereby the light directed at said first detecting element and focused thereon has a different wavelength from the light directed at said second detector element and focused thereon, said refractive-diffractive optical element being arranged in a ray path between the area in which the interaction takes place between the gas to be analyzed and the measuring light and the detector arrangement; and means for setting the temperature of said at least one refractive-diffractive optical element or for maintaining said refractive-diffractive optical element at presettable values.

22. A device in accordance with claim 13, wherein said first emitted light wavelength detection range is different from said second emitted light wavelength detection range.

23. A device in accordance with claim 13, wherein said light directed at said first detector element and focused thereon has a different wavelength from said light directed at said second detector element and focused thereon.

* * * * *